United States Patent [19]
Chester et al.

[11] Patent Number: 5,350,059
[45] Date of Patent: Sep. 27, 1994

[54] DENTAL DISPENSING SYSTEM

[75] Inventors: Bruce E. Chester, Irvine; James D. Cleary, Glendora, both of Calif.

[73] Assignee: Minnesota Mining and Manufacturing Company, St. Paul, Minn.

[21] Appl. No.: 12,304

[22] Filed: Feb. 2, 1993

[51] Int. Cl.$^5$ ............................................. A61B 19/02
[52] U.S. Cl. ................... 206/63.5; 206/460; 206/526; 206/565; 206/820; 433/9
[58] Field of Search ............ 206/63.5, 330, 345, 206/368, 477, 483, 460, 526, 560, 565, 820; 433/9

[56] References Cited

U.S. PATENT DOCUMENTS

| | | | |
|---|---|---|---|
| 3,250,003 | 5/1966 | Collito | 32/14 |
| 3,378,925 | 4/1968 | Faller | 206/63.5 |
| 3,698,547 | 10/1972 | Roberts et al. | 206/460 |
| 4,055,249 | 10/1977 | Kojima | 206/820 |
| 4,204,325 | 5/1980 | Kaelble | 433/9 |
| 4,817,805 | 4/1989 | Rodriquez | 206/482 |
| 4,903,840 | 2/1990 | So | 206/581 |
| 4,948,367 | 8/1990 | Haas | 433/9 |
| 4,952,204 | 8/1990 | Korteweg | 604/1 |
| 4,979,611 | 12/1990 | Bolliger et al. | 206/83 |
| 5,015,180 | 5/1991 | Randklev | 433/9 |
| 5,172,809 | 12/1992 | Jacobs et al. | 206/368 |
| 5,183,403 | 2/1993 | Masuhara et al. | 433/9 |
| 5,221,202 | 6/1993 | James | 206/63.5 |

FOREIGN PATENT DOCUMENTS

PCT/JP89/0-1109  5/1991  Japan.
WO92/08419  5/1992  PCT Int'l Appl..

OTHER PUBLICATIONS

3M Unitek Catalog pp. 5-9 and 5-19, 1990.

Primary Examiner—David T. Fidei
Attorney, Agent, or Firm—Gary L. Griswold; Walter N. Kirn; James D. Christoff

[57] ABSTRACT

A dispensing system for dental appliances such as orthodontic brackets includes a plurality of containers releasably connected to a carrier strip. The carrier strip is received in channels of an organizer tray that hold the carrier strip in place as individual containers are detached from the carrier strip. Individual containers, each containing a dental appliance, are selected and removed from the organizer tray for placement in a patient setup tray that is then carried to the patient's chair.

19 Claims, 11 Drawing Sheets

DENTAL DISPENSING SYSTEM

BACKGROUND OF THE INVENTION

1. Field of the Invention

This invention relates to a dental dispensing system especially useful for dispensing individually packaged dental appliances such as orthodontic brackets.

2. Description of the Related Art

In orthodontic treatment, a set of dental appliances (commonly called "braces") is utilized to move malpositioned teeth to orthodontically correct positions. The appliances typically include tiny brackets that are connected to the patient's teeth. An archwire is secured in a slot of the brackets and functions as a track to guide movement of the brackets to shift the associated teeth to desired positions.

Orthodontic brackets are often bonded directly to the tooth surfaces using an adhesive that cures after a predetermined amount of time, or using an adhesive that cures upon exposure to light. Light curable adhesives are advantageous because the bracket may be placed on the tooth and precisely positioned as necessary before the curing lamp is activated to fix the bracket in place.

Recent advances in the field of direct bonded dental articles including orthodontic brackets are described in U.S. Pat. Nos. 5,015,180 and 4,978,007, as well as pending U.S. patent application Ser. No. 07/826,225, all of which are assigned to the assignee of the present invention. U.S. Pat. No. 5,015,180 describes in one embodiment an orthodontic bracket and a light curable paste sandwiched between a base of the bracket and a flexible, releasably adhering cover sheet. To bond the bracket to a tooth, the cover sheet is removed from the paste and the bracket base is then applied to the tooth. Such construction represents a time savings for the orthodontist, because the orthodontist need not dispense and apply the adhesive paste to the bracket base before bonding the bracket to the tooth.

U.S. Pat. No. 4,978,007 and the aforementioned pending U.S. patent application Ser. No. 07/826,225 describe a packaged dental appliance that is precoated with adhesive and is received in a well or recess of a container that protects the adhesive from light, oxygen, water vapor and contaminants. The appliance is preferably retained in the recess in an upright manner that facilitates grasping of the sides of the appliance by a placement instrument or other tool so that the appliance may be removed from the container and placed directly on the surface of the chosen tooth.

Pending U.S. patent application Ser. No. 07/826,225 describes a box having two rows of holes for receiving containers that contain individual precoated appliances. The box is useful as a shipping carton for transporting a set of appliances from the manufacturer to the orthodontist, and is also useful as a setup tray that may be placed next to the patient's chair when it is desired to affix the appliances to the patient's teeth. Each hole in the box corresponds to a certain tooth in the mouth, and the containers having particular appliances are selected ahead of time and placed in the proper holes in the box in an array corresponding to the tooth locations on which each appliance is to be applied.

The containers containing appliances as described in pending U.S. patent application Ser. No. 07/826,225 can be selected and placed in proper positions in the box either by the manufacturer, or by the orthodontist or orthodontist's staff. Many orthodontists prefer to retain a stock of various brackets for placement in the box to avoid the need for placing a custom order with the manufacturer each time orthodontic treatment is initiated. However, the characteristics of maloccluded teeth and the resultant treatment techniques vary widely, and as a result the set of brackets prescribed for one patient may vary from the set of brackets prescribed for another patient.

Orthodontists who prefer to retain a variety of orthodontic brackets on hand for making a customized patient "kit" or set of brackets are thus faced with the problem of keeping a sufficient number and variety of brackets on hand to meet the foreseen needs of each patient. However, storage space in offices is often at a premium. Moreover, unless the stock is well organized, it is sometimes difficult to quickly find a particular bracket or to ascertain whether or not additional brackets of a particular type should be reordered to retain sufficient stock on hand.

SUMMARY OF THE INVENTION

The present invention relates to a dental dispensing system and, in one embodiment, comprises a plurality of dental appliances, and a plurality of containers each receiving a respective one of the dental appliances. The system further includes a carrier strip and means for releasably connecting each of the containers to the carrier strip. The system includes an organizer tray, and structure releasably securing the carrier strip to the organizer tray such that the carrier strip is retained by the organizer tray as one or more of the containers are released from the carrier strip.

In another embodiment, the present invention is directed to a dental dispensing system that comprises a plurality of dental appliances and a plurality of containers. Each of the containers has a sidewall and a bottom defining a well, and the well of each of the containers receives a respective one of the dental appliances. Each of the containers includes a cover removably covering its well, and each of the containers has a generally flat configuration. The system also includes a carrier strip and means for detachably connecting each of the containers to the carrier strip such that the containers are oriented in a stacked array with each of the containers oriented in an upward direction.

Another aspect of the present invention concerns a dental dispensing system that comprises a plurality of dental appliances and a plurality of containers each having a sidewall and a bottom defining a well. Each of the containers includes a cover extending across the well, and the cover includes an outwardly projecting tab for opening the cover for access to the well. Each well receives a respective one of the dental appliances. The system also includes a carrier strip and a quantity of adhesive detachably connecting the tab of each container to the carrier strip in order to releasably retain each container on the carrier strip.

The invention also concerns a dental setup tray having a series of holes. The setup tray is made of a flexible, rubbery material.

The invention is also directed to a dental setup tray having a series of holes, wherein the setup tray is made of a crosslinked elastomeric material having a glass transition temperature below its temperature of use.

DETAILED DESCRIPTION OF THE PREFERRED EMBODIMENTS

Figure 5:
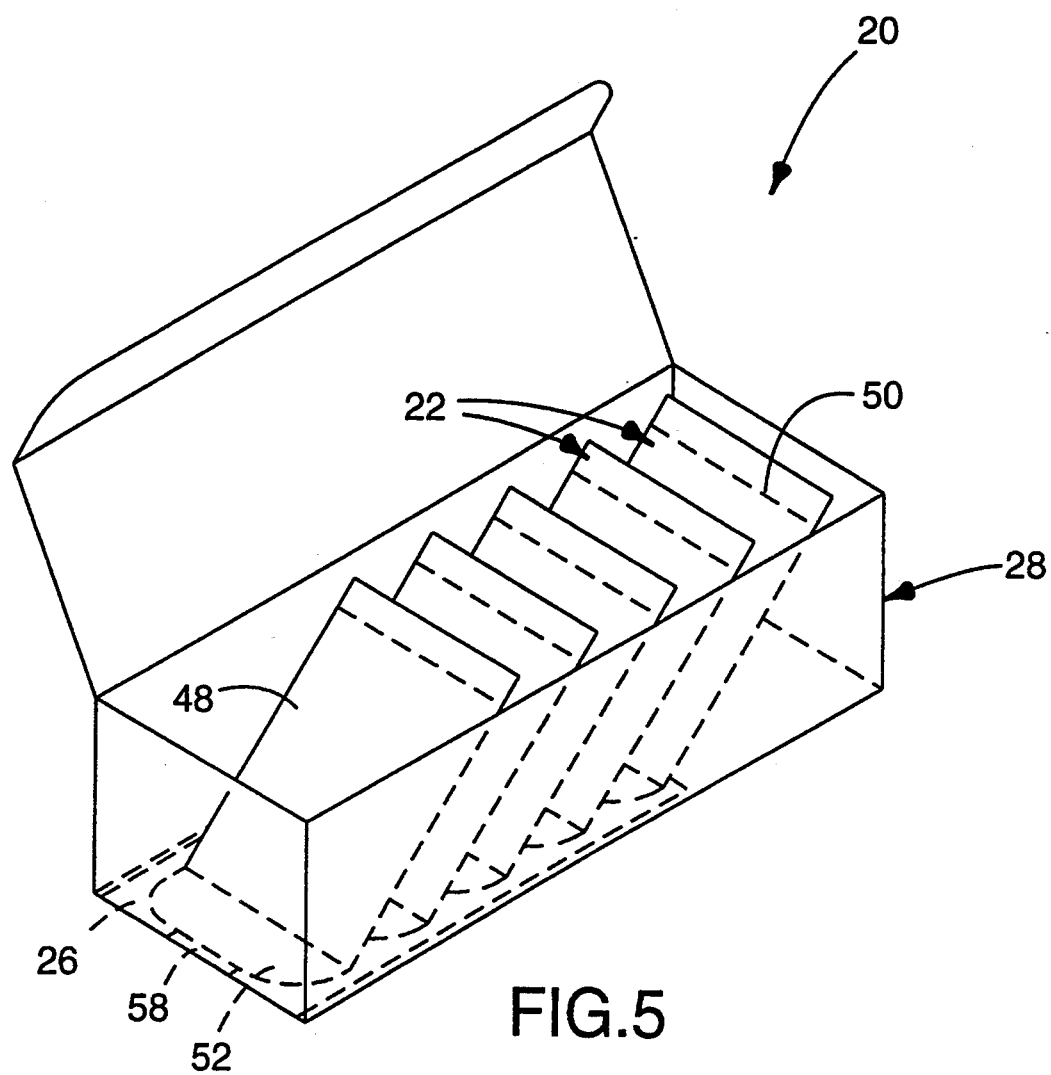
FIG. 5 is a reduced perspective view of the containers and carrier strip shown in FIGS. 3 and 4 as received in a sales unit carton.
Figure 9:
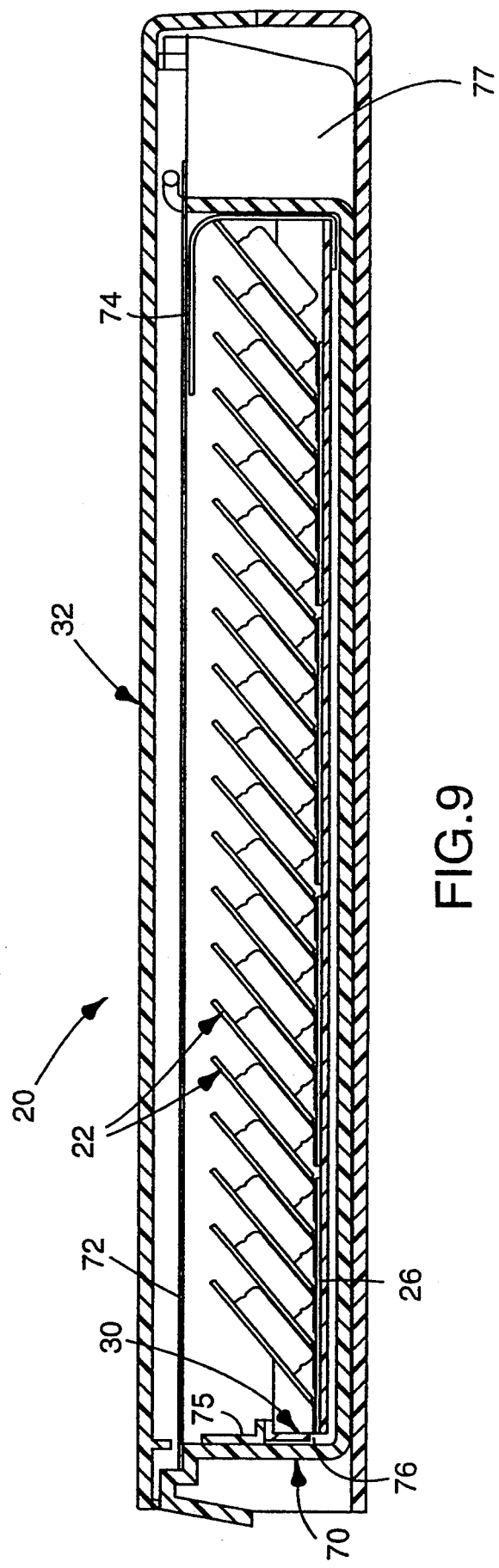
FIG. 9 is an enlarged, side cross-sectional view of the organizer tray and storage cabinet shown in FIG. 7 (with a flange of a rib of the organizer try removed for purposes of illustration)
Figure 10:
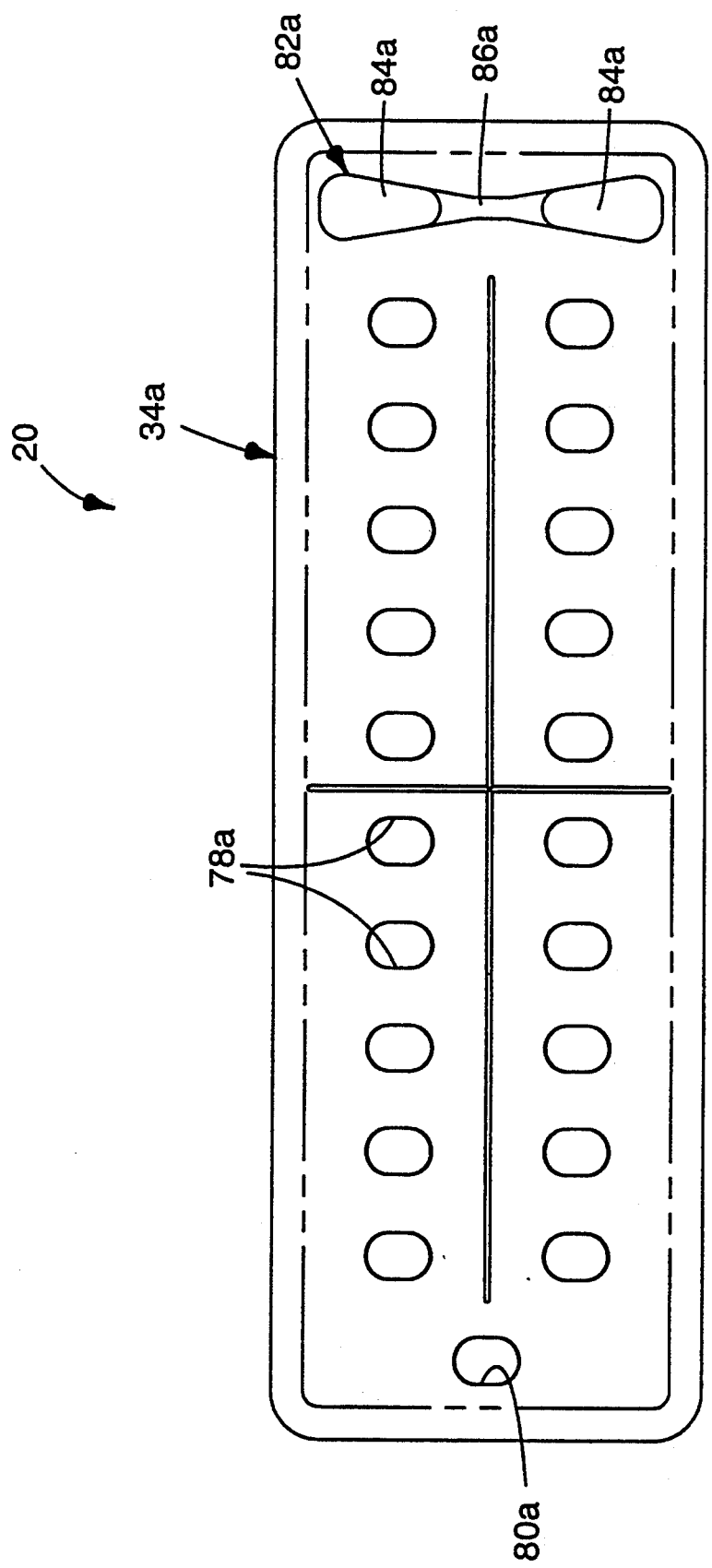
FIG. 10 is a reduced plan view of a patient setup tray according to one embodiment of the dental dispensing system of the present invention.
Figure 11:
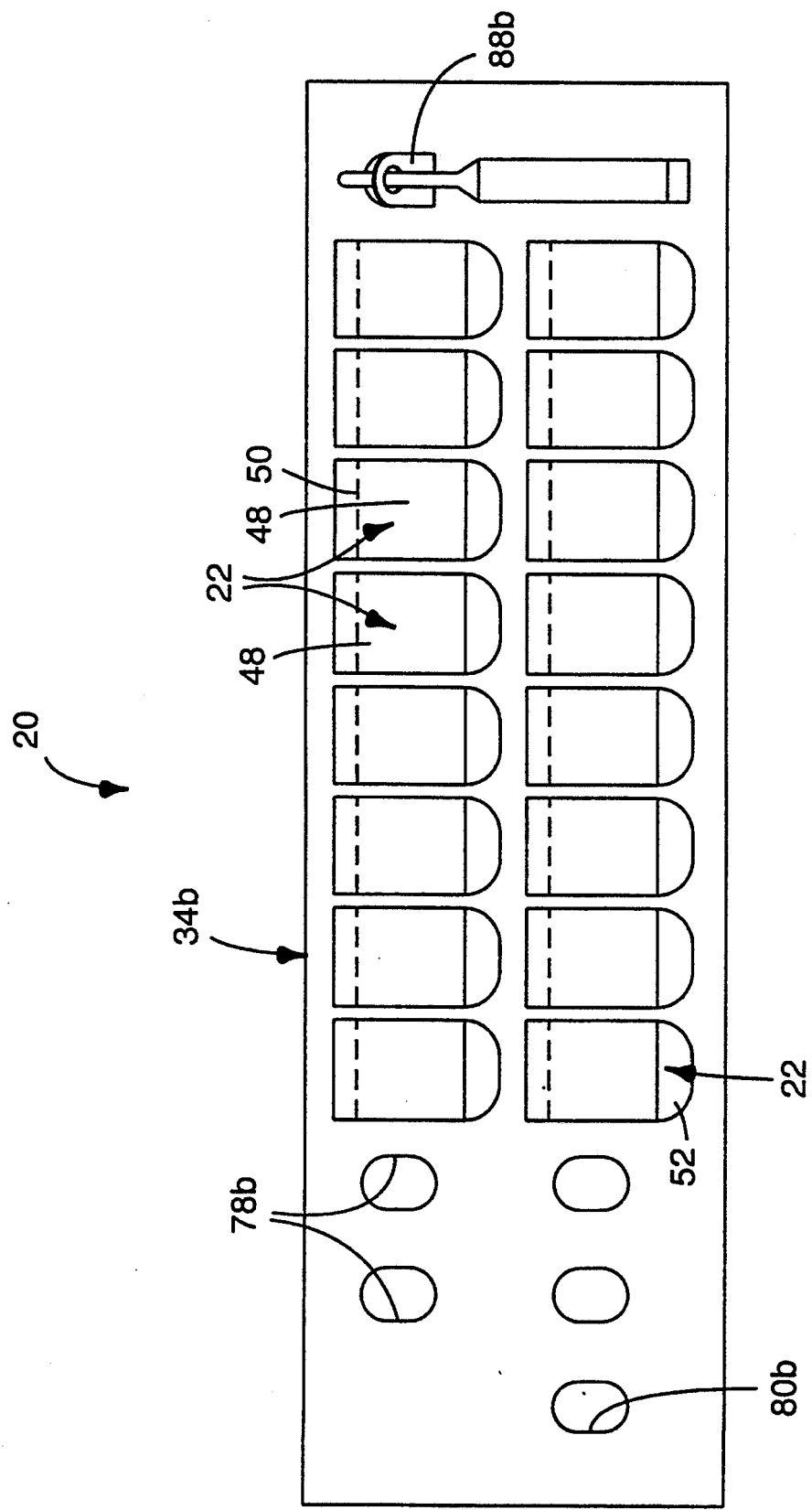
FIG. 11 is a reduced plan view of a patient setup tray in accordance with another embodiment of the invention.
Figure 12:
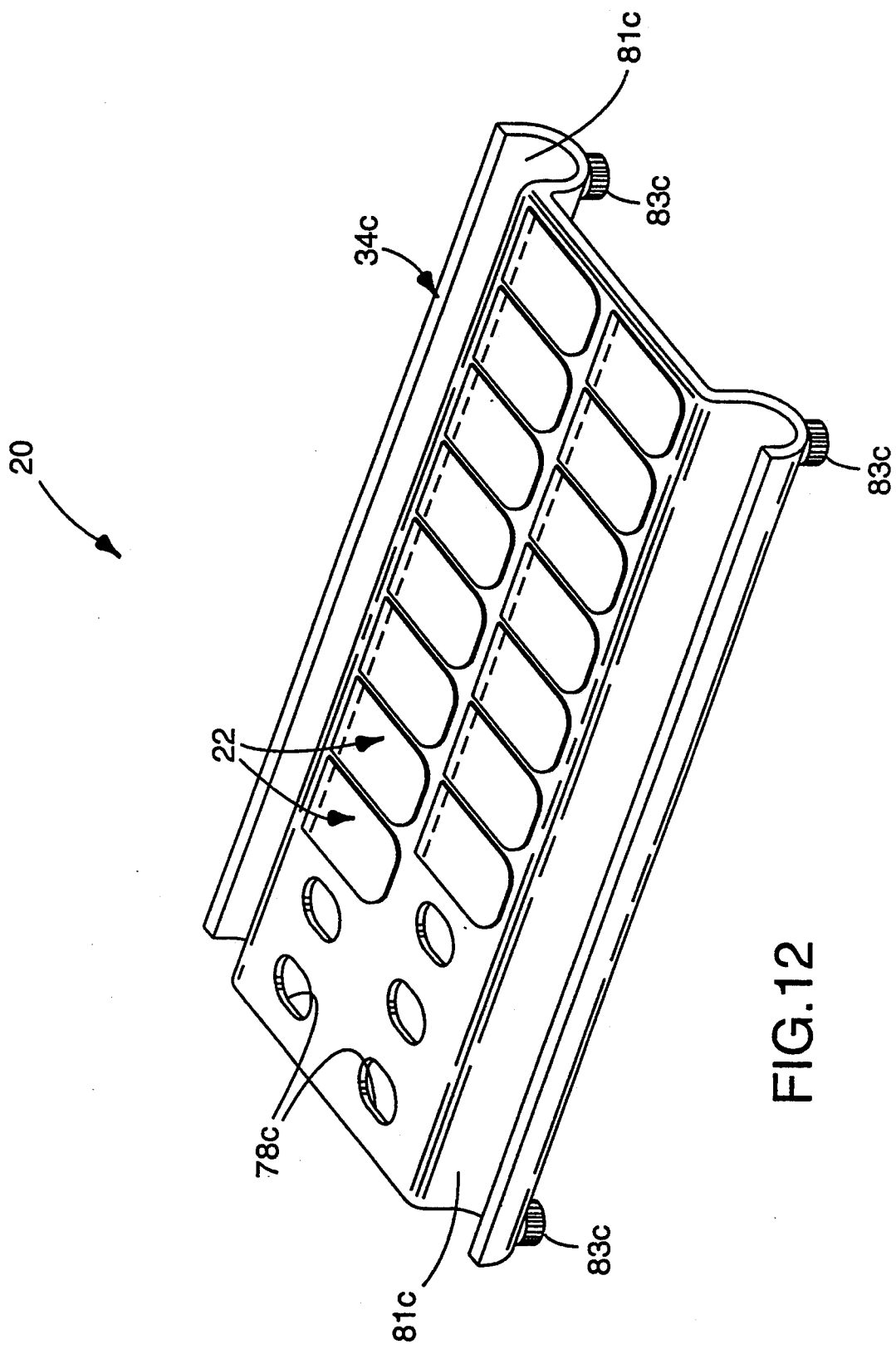
FIG. 12 is a reduced perspective view of a patient setup tray in accordance with another embodiment of the invention.

A dental dispensing system 20 is illustrated in FIGS. 1-14 and broadly includes a plurality of containers 22, a plurality of dental appliances (such as the orthodontic bracket appliance 24 shown in FIG. 2) and a carrier strip 26 shown in FIGS. 3-6. A sales unit carton 28 is illustrated in FIG. 5, an organizer tray 30 is shown in FIGS. 6-9, a modular storage cabinet 32 is illustrated in FIGS. 7 and 9, and 35 patient setup trays 34a, 34b, 34c according to different embodiments are shown in FIGS. 10-12.

Figure 1:
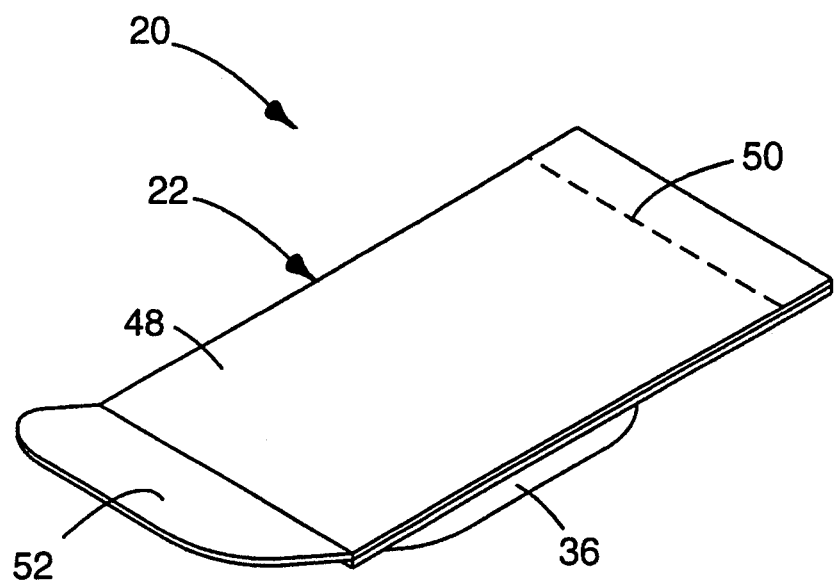
FIG. 1 is a perspective view of a container of a dental dispensing system constructed in accordance with the invention, wherein a cover of the container is shown in a closed position.
Figure 2:
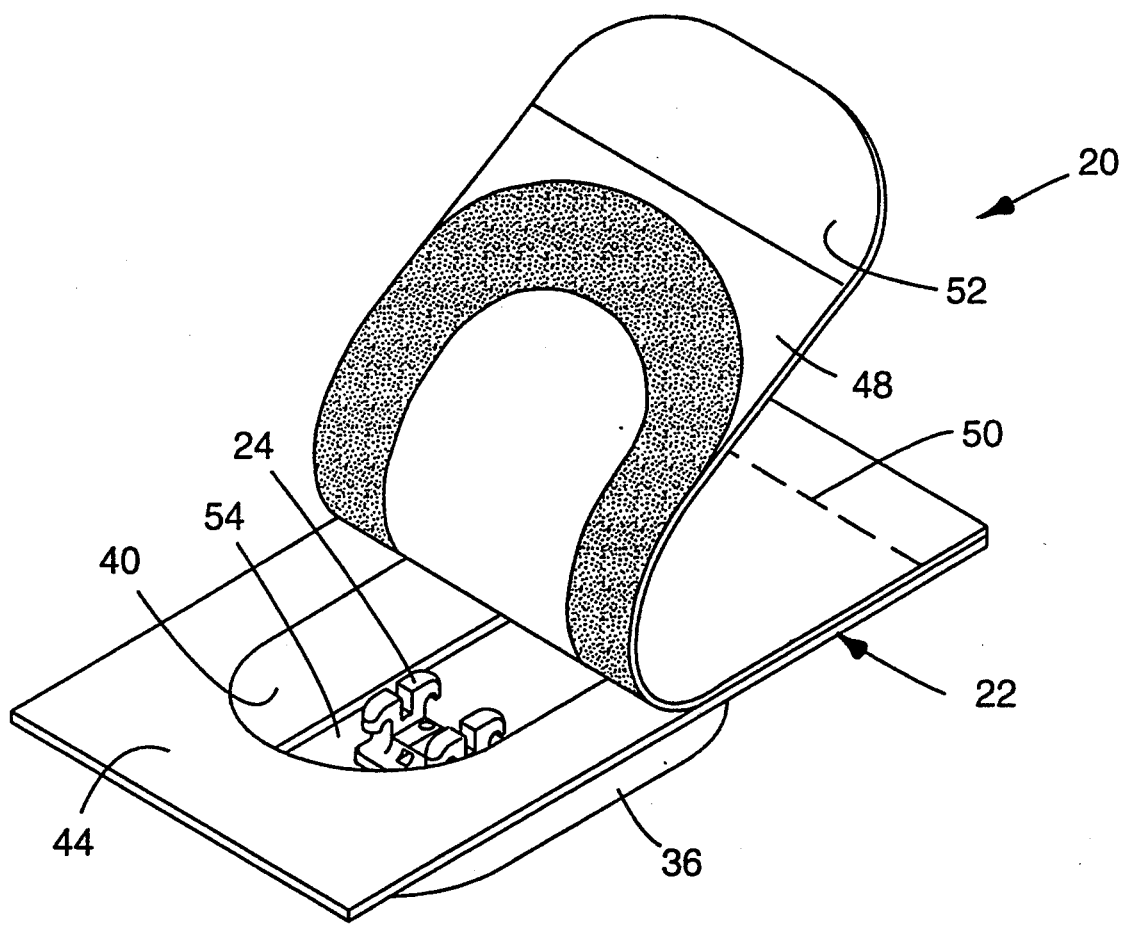
FIG. 2 is an enlarged view somewhat similar to FIG. 1 except that the cover has been opened to reveal a dental bracket appliance received in a well of the container.
Figure 3:
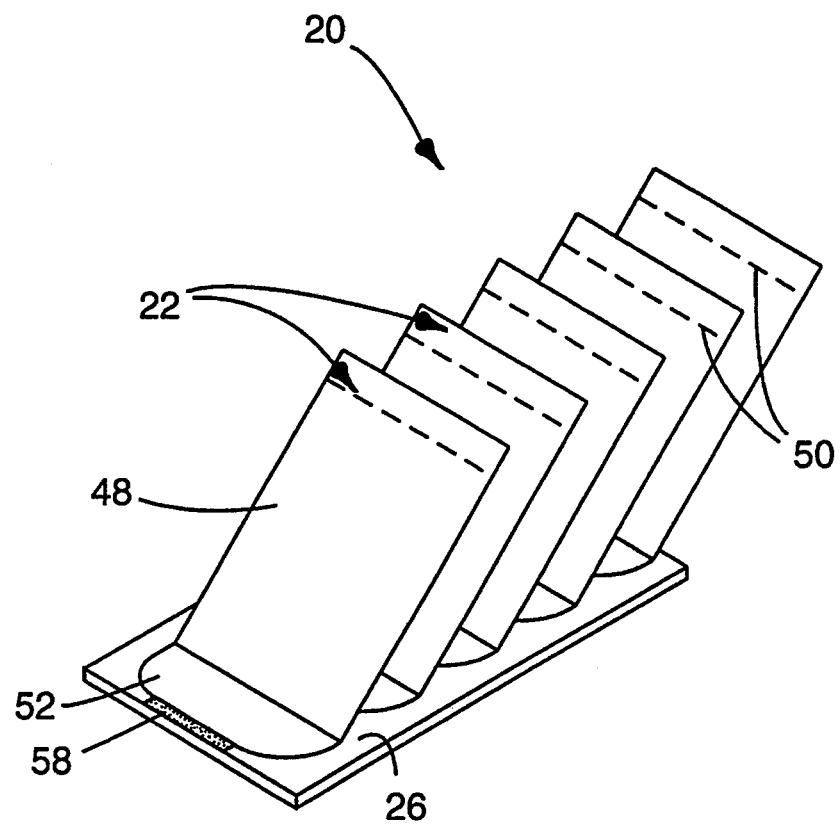
FIG. 3 is a reduced perspective view of a plurality of containers such as shown in FIGS. 1 and 2, each of which is detachably mounted on a carrier strip.
Figure 4:
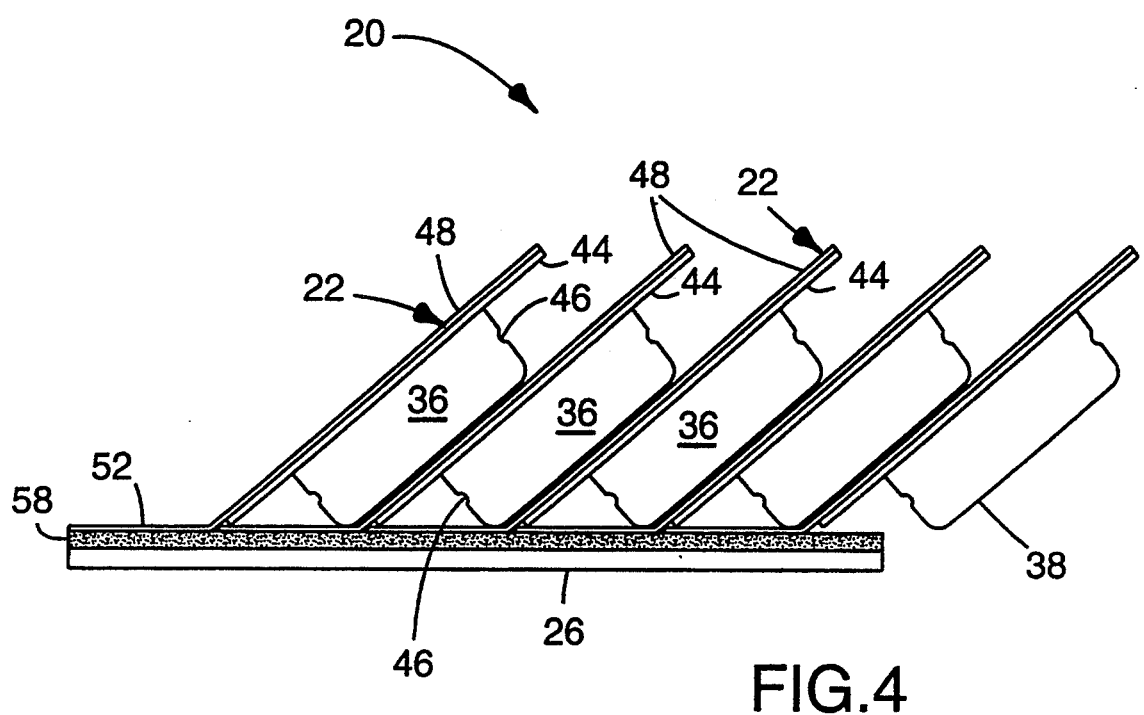
FIG. 4 is an enlarged side elevational view of the containers and carrier strip shown in FIG. 3.

In more detail, the containers 22 each include an upright sidewall 36 that defines an oval in plan view, and an oval-shaped bottom 38 (FIG. 4) is connected to the sidewall 36. The sidewall 36 and the bottom 38 together define a well 40 as illustrated in FIG. 2 to receive the bracket appliance 24. The sidewall 36 is also connected to a rectangular top flange 44 having a central, oval-shaped opening over the well 40. Additionally, the sidewall 36 has a pair of opposed, inwardly extending recesses 46 as can be viewed in FIG. 4.

The sidewall 36, bottom 38 and top flange 44 are integrally formed from a sheet of flexible material that provides a substantial barrier to the transmission of light, oxygen and water vapor. Preferably, the sheet of flexible material forming the sidewall 36, bottom 38 and top flange 44 is black 0.33 mm thick polyethylene terephthalate glycol ("KODAR" brand PETG no. 6763, Kodak Chemical Company) that is treated with a silicone release agent (no. 24, Dow Chemical).

Each of the containers 22 includes a cover 48 to initially close the well 40. The cover 48 comprises a top film ("COMPUCAL II" brand, Flexcon Company, Inc., Spencer, Mass.; from ACUTEK of Inglewood, Calif., catalog no. ACTK 020) made of a 0.025 mm clear polyester film carrying an adhesive (no. 517, Flexcon) and covered by a printable matte topcoat, intermediate film made of a 0.13 mm polyester sheet having a metallized surface (0.05 mm thick) of aluminum bonded (by the no. 517 adhesive mentioned above) to the top clear polyester film, and a double coated lower film assembly (no. ACTK 023, Acutek) that comprises a high tack, non-repositionable 0.018-0.02 mm thick layer of acrylic pressure sensitive adhesive (no. H529, Flexcon), a 0.025 mm thick polyester carrier film and a 0.018-0.02 mm thick layer of low tack, repositionable acrylic pressure sensitive adhesive (no. H558, Flexcon).

As an alternative, the top film of the cover 48 is Flexcon's impact printable film no. TC 374/L-23 (from Acutek). As another option, the top film is 3M's matte transparent acetate film assembly no. 7701. An option for the intermediate film is Flexcon's "DERMAFLEX" brand polyester and aluminum foil assembly no. MF 335.

The top film and intermediate film extend the full length and width of the cover 48, and the non-repositionable adhesive, the carrier film and the repositionable adhesive are die cut to form an oval and adjacent endmost rectangular section. The central portion of the oval is removed and matches the shape of the well 40, such that the repositionable adhesive contacts only the top flange 44 and does not extend across the well 40; rather, the well 40 when closed by the cover 48 is covered by an exposed portion of the intermediate film.

The cover 48 includes a line of perforations 50 that defines a rear hinge portion. Good results have been observed when the cover 48 has an overall width of 1.8 cm, and is provided with two perforations of 0.55±0.01 cm each and two perforations of 0.25±0.01 cm each, presenting three lands of 0.06±0.01 cm each, so that the ratio of total perforation length to land length is about 9 to 1. The perforations extend completely through the cover 48.

The cover 48 includes a front, inclined tab 52 that extends away from the well 40. The tab 52 provides a convenient handle for grasping the cover 48 and moving the cover 48 in the manner shown in FIG. 2 toward an open, upstanding position, bent at the line of perforations 50. The line of perforations 50 facilitate self-retention of the cover 48 in its open, upright position and permit the cover 48 to be made of relatively stiff materials.

A flexible film 54 (FIG. 2) having an oval configuration matching the shape of the sidewall 36 is received in the well 40. Preferably, the film 54 is 0.02 mm thick sheet of clear oriented polyester film Type A that is fixed by an acrylic pressure sensitive adhesive (no. H529, Flexcon) to the bottom 38. Alternatively, the film 54 is made of a 0.05 mm thick sheet of fluorinated ethylene propylene copolymer ("TEFLON" brand FEP no. 200 C, clear, E. I. du Pont de Nemours & Co.) that is etched on one side by electrostatic discharge apparatus to enhance the pond to the acrylic pressure sensitive adhesive (no. H529, Flexcon) that secures the film 54 to the bottom 38.

The bracket appliance 24 is adapted to be bonded directly to the tooth surface, and appropriately has an exterior base surface with a concave, compound contour to match the contour of the tooth. The appliance 24 may be made of a translucent ceramic material or of other material such as metal, glass or plastic. The base of the appliance 24 is precoated with a light-curable, non-toxic orthodontic adhesive such as that described in co-pending U.S. patent application Ser. No. 07/902,444, the disclosure of which is incorporated by reference herein.

A first end section of the film 54 contacts the adhesive precoated on the appliance 24. The first end section is substantially free of direct connection to the container bottom 38 and is therefore somewhat unrestrained. However, a second end section of the film 54 remote from the first end section and the appliance 24 is in engagement with the pressure sensitive adhesive that secures the film 54 to the bottom 38. As such, as the appliance 24 is lifted from the well 40, the first section of the film 54 moves away from the bottom 38 while the second section of the film 54 remains fixed to the bottom 38, enabling the film 54 to peel away from the adhesive precoated on the appliance 24 in order to facilitate separation of the adhesive from the film 54 and enabling such adhesive to remain substantially undisturbed and in contact with the base of the appliance 24.

Further details and additional alternative materials relating to the film 54, the bracket appliance 24, the container 22 (including the cover 48) and the film 54 are found in the aforementioned copending U.S. patent application Ser. No. 07/826,225 and/or pending U.S. patent application Ser. No. 07/615,702, the disclosures of both of which are expressly incorporated into the present disclosure.

As illustrated in FIGS. 3–6, the carrier strip 26 comprises a flat, rectangular section of 0.5 mm thick solid bleached sulfate paperboard that is clay coated on one side and that carries a quantity of hot melt adhesive 58. The adhesive 58 extends in a continuous bead centrally along the longitudinal axis of the upper, clay coated side of the carrier strip 26, although an interrupted bead, a series of dots or other pattern is also possible.

A row of aligned containers 22 is arranged in an array as shown in FIGS. 3–7 atop the carrier strip 26, with each of the containers 22 extending in a non-horizontal, upward direction. The adhesive 58 serves as a means for detachably connecting each of the containers 22 to the carrier strip 26. The adhesive 58 is removably bonded to the underside of the tab 52 of each of the containers 22, and the bottom 38 of all of the containers 22 (except for the rearmost container 22) rests against the top face of the cover 48 of the succeeding container 22.

The currently preferred adhesive 58 is no. 3748 TC (from 3M Company) although other hot melt adhesives are also possible such as nos. 3747 TC, 3762 TC and 3792 TC (3M). The tab 52 may optionally be diecut to provide an aperture to allow the adhesive 58 to flow into the aperture and to facilitate retention of the tab 52 to the adhesive. Alternatively, the adhesive 58 may be a double sided acrylic or rubber based adhesive tape such as nos. 9425, 9495, 9820, 9851 and 665 (3M). If a double sided adhesive tape is utilized, the tape preferably has a high tack adhesive on one face in contact with the carrier strip 26, and a low tack adhesive on the opposite face (i.e., facing upwardly and away from the carrier strip 26). Other means for detachably connecting the containers 22 to the carrier strip 26 are also possible, such as ultrasonic or vibration bonding, induction heat bonding or a mechanical interlock.

The sales unit carton 28 that is shown in FIG. 5 serves as a shipping box for the assembly of the containers 22 and the carrier strip 26. The carton 28 is made of 0.45 mm thick clay coated solid bleached sulfate paperboard, and is preferably provided with a tamper evident seal ("SCOTCHMARK" brand no. 7110, 3M) (not shown) extending across an end sidewall and both a top and bottom lid of the carton 28. The tamper evident seal also carries identification such as Palmer notation (that identifies the tooth for which the appliance is intended), catalog numbers and other descriptive information, and also provides a substrate for carrying a high-temperature warning indicator.

When the assembly of the carrier strip 26 and the containers 22 is placed in the sales unit carton 28, the front edge of the carrier strip 26 contacts a lower corner of one end of the carton 28 while the upper edge of the top flange 44 of the rearmost container 22 is closely adjacent the upper corner an opposite end of the carton 28. The carton 28 rectangular to facilitate shipping, storage and handling, and yet provides a relatively compact protective enclosure for the containers 22.

The organizer tray 30 that is depicted in FIGS. 6–9 has a generally planar configuration with a flat horizontal bottom assembled wall 60 and a flat vertical front wall 62. As shown for example in FIGS. 6 and 8, the organizer tray 30 also includes a series of spaced apart upright ribs 64 that extend in a perpendicular direction away from the front wall 62. A pair of opposed, horizontal flanges 66 (FIG. 8) extend along the length of adjacent pairs of the ribs 64 to define a pair of opposed channels 68 between the flanges 66 and the bottom wall 60.

Figure 6:
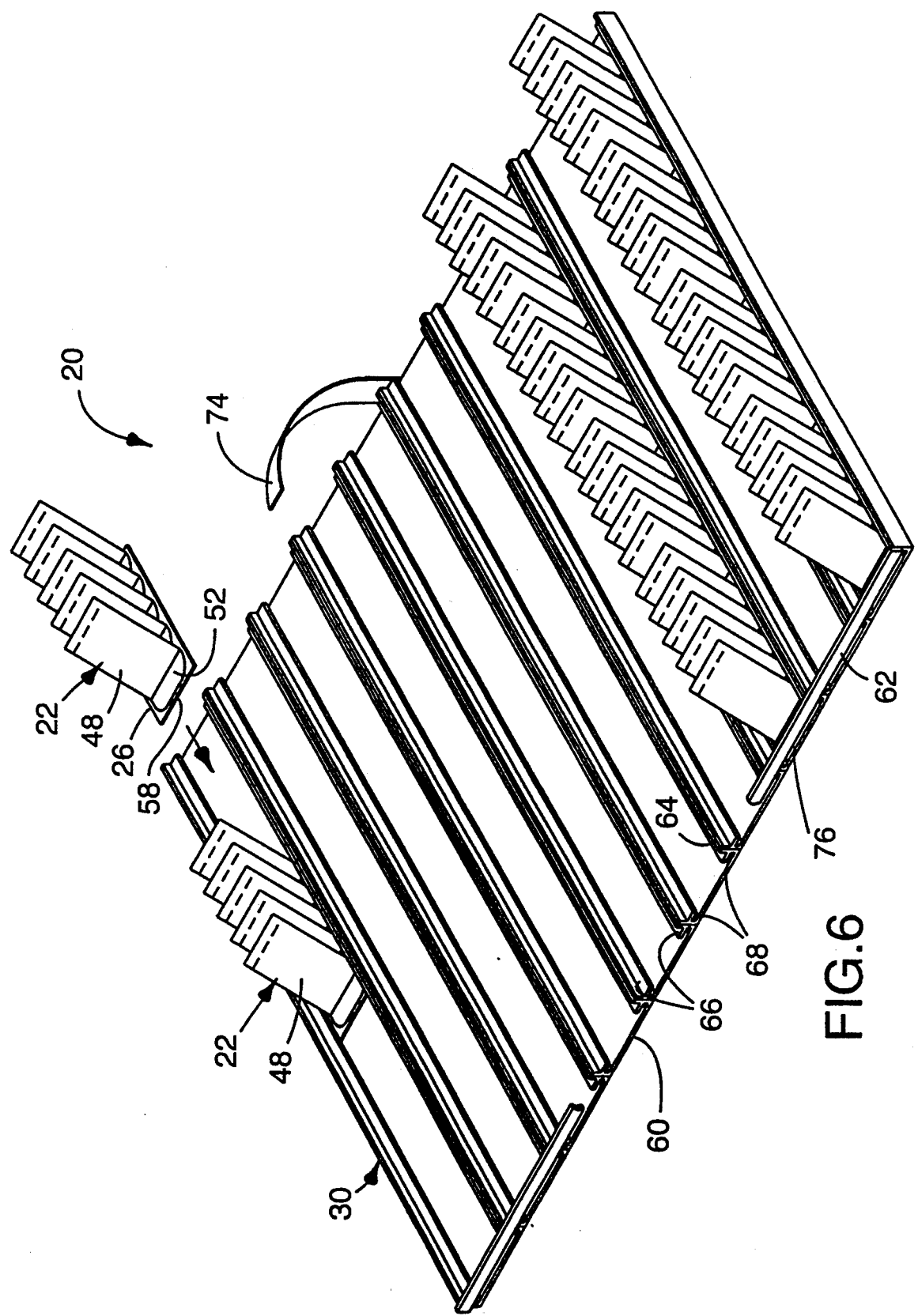
FIG. 6 is a reduced perspective view with parts broken away in section of an organizer tray of the present invention, wherein a number of carrier strip and container assemblies such as shown in FIGS. 3-5 are removably received in the tray.
Figure 7:
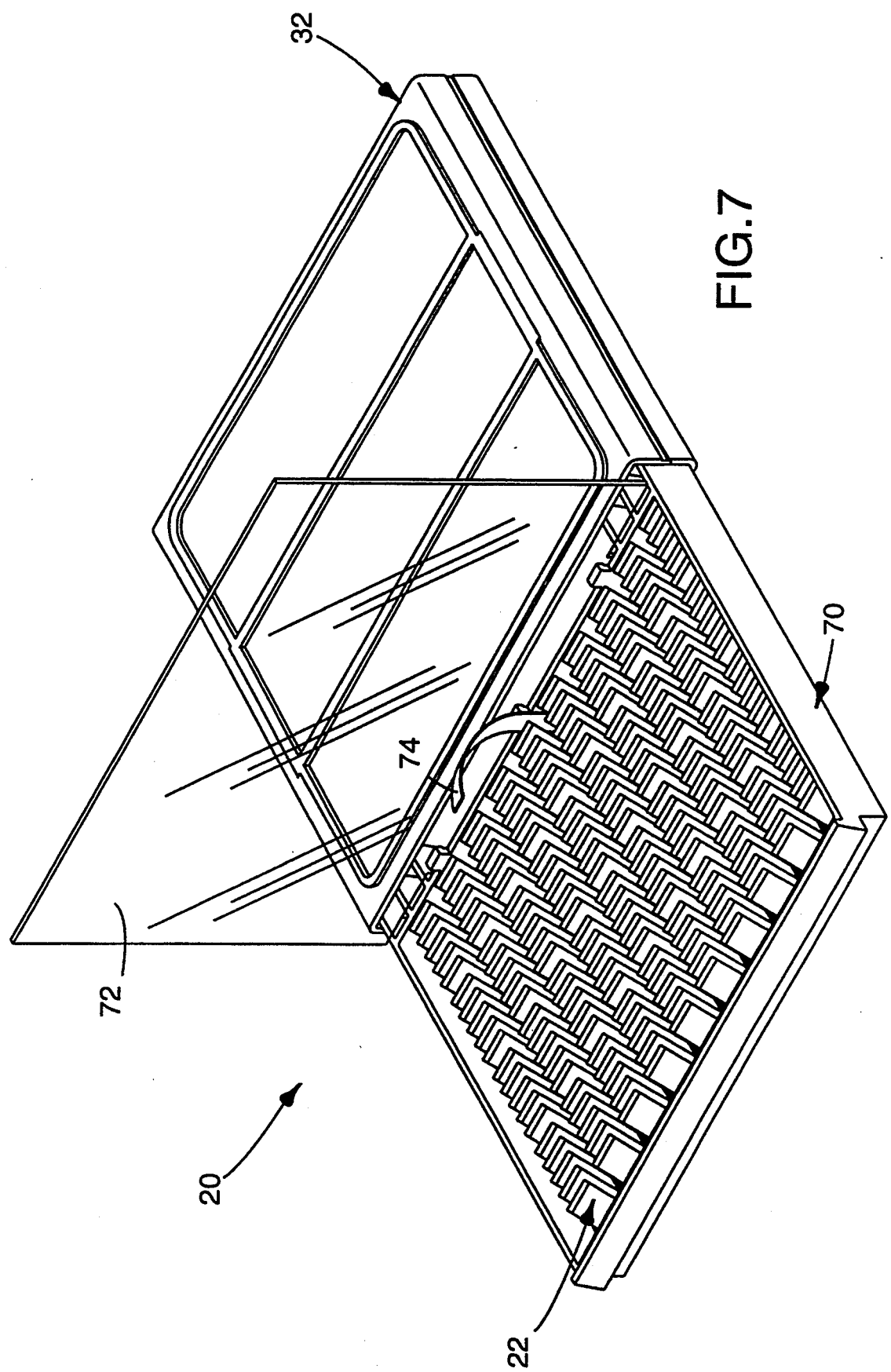
FIG. 7 is a reduced perspective view of the organizer tray shown in FIG. 6 except that the tray is filled with container and carrier strip assemblies and the tray is supported by a drawer of a modular storage cabinet.

The channels 68 are spaced apart a sufficient distance to matably and slidably receive the elongated side edge portions of the carrier strip 26 in the manner indicated by the arrow in FIG. 6. Preferably the rear end of the flanges 66 is chamfered and the front, leading edge of the carrier strip 26 is also chamfered in order to facilitate insertion of the carrier strip 26 into the channels 68. The organizer tray 30 has ten aligned, side-by-side pairs of channels 68, advantageously corresponding to ten respective, expected locations of use of the corresponding bracket appliances 24 in one arch of the mouth.

FIG. 7 is an illustration representative of the appearance of the organizer tray 30 and the containers 22 once all of the channels 68 of the organizer tray 30 have been filled with the assemblies of the containers 22 and the carrier strips 26. The organizer tray 30 as depicted in FIG. 7 is received in a drawer 70 of the modular storage cabinet 32. A dust cover 72 has three rear holes that are connected to loop-style hinges of the drawer 70 and is made of a plastic sheet material that is transparent to light in the visible spectrum. (As an alternative, the cover 72 could be opaque to actinic radiation.) Optionally, the hinges have a lateral notch to releasably retain the dust cover 72 in the upright position shown in FIG. 7. The cabinet 32, the drawer 70 and dust cover 72 (but without the organizer tray 30) are similar to an orthodontic band cabinet assembly available from a subsidiary of the assignee of the present invention (no. 30970-0007, 3M Unitek).

When it is desired to remove one or more containers 22 from the drawer 70, the selected containers 22 are grasped and pulled or peeled in an upward direction away from the drawer 70 until the tab 52 releases from the adhesive 58. The channels 68 provide structure releasably securing the carrier strip 26 to the organizer tray 30 such that the carrier strip 26 is retained by the organizer tray 30 as one or more of the containers 22 are released from the carrier strip 26. Advantageously, as each container 22 is removed from the drawer 70, descriptive information such as catalog numbers and Palmer notation that is printed on the cover 48 of the following container 22 comes into immediate view, so that the containers 22 are well organized and the proper containers 22 can be quickly selected at all times.

When it is desired to replenish the supply of containers 22 in the organizer tray 30, the organizer tray 30 is lifted from the drawer 70 by gripping a length of flexible plastic pull strip 74 that is secured to the underside of the bottom wall 60. As illustrated in FIG. 9, an attached shoulder 75 extends along the inner surface of the front wall of the drawer 70 in order to retain the organizer tray 30 horizontally in place and flatly against the bottom of the drawer 70 as the containers 22 are detached from the carrier strip 26. However, the organizer tray 30 may be removed from the drawer 70 by grasping the pull strip 74 to slightly move the rear edge of the organizer tray 30 in an upward direction, and then in a rearward direction away from the shoulder 75. Once the front wall 62 clears the shoulder 75, the organizer tray 30 may be pulled upwardly and out of drawer 70.

Figure 8:
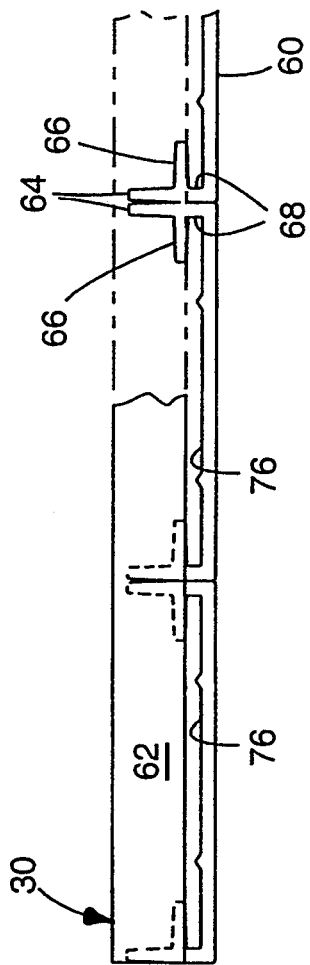
FIG. 8 is an enlarged, fragmentary, front elevational view of the organizer tray alone that is shown in FIGS. 6 and 7, with part of a front wall broken away.

As can be observed in FIGS. 6 and 8, the front wall 62 of the organizer tray 30 is spaced a slight distance from the bottom wall 60 in order to present a slot 76 that extends between all of the channels 68 above the bottom wall 60. The slot 76 is of a height approximately equal to the height of the channels 68. Once all of the containers 22 have been removed from the carrier strip 26, and once the organizer tray 30 has been lifted from the cabinet drawer 70, the empty carrier strips 26 slide through the adjacent portion of the slot 76 at the front end of the channels 68, thereby enabling the removal of the empty carrier strips 26 from the organizer tray 30 without removing any following carrier strips 26 that are still connected to containers 22.

New assemblies of containers 22 and carrier strips 26 are inserted into the channels 68 from the opposite, rear side of the organizer tray 30. As such, the user can be assured that the stock is continuously rotated in first-in, first-out procedure since older stock is advanced toward the front of the organizer tray 30 as newer stock is inserted through the rear of the organizer tray 30. Advantageously, the front wall 62 blocks the entry of new assemblies of carrier strips 26 and containers 22 into the channels 68 so that proper rotation of the stock is carried out.

Preferably, at least part of the descriptive information (such as a catalog number) that is printed on the covers 48 is also printed in identical fashion on the bottom of the associated carrier strips 26. Consequently, once all of the containers 22 have been detached from the carrier strip 26, the empty carrier strip 26 serves as convenient reorder card that may be retained as a record for ease in reordering additional stock. If the adhesive 58 is repositionable, the empty carrier strip 26 may be temporarily lodged on the dust cover 72 or another convenient location.

When not in use, the storage cabinet 32 may be closed by sliding the drawer 70 toward the rear of the storage cabinet 32 until the drawer 70 reaches the position shown in FIG. 9. The dust cover 72 lays flatly against an upwardly facing surface of the drawer 70 when the drawer 70 is closed. A pair of rearwardly extending arms 77 connected to the drawer 70 have upwardly extending flanges that engage respective inner wall sections located above the front opening of the storage cabinet 32 in order to substantially prevent inadvertent detachment of the drawer 70 from the cabinet 32 when the drawer 70 is opened.

The patient setup tray 34a that is illustrated in FIG. 10 is useful for holding in an organized fashion a number of containers 22 (with the appliances 24 therein) that have been selected and removed from the organizer tray 30 for use on a patient. To this end, the setup tray 34a has a series of oval holes 78a that are configured to matingly receive the sidewall 36 of each selected container 22. The holes 78a preferably are slightly smaller than the shape of the sidewall 36 so that a slight interference fit is established in order to releasably retain the containers 22 in the setup tray 34a. An opposed pair of projections is located in each hole 78a for snap-fit engagement with the recesses 46.

The holes 78a are arranged along two rows of ten holes 78a that correspond to respective teeth of the dental arch and to the ten pairs of channels 68 of the organizer tray 30. For convenience purposes, Palmer notation or other indicia may be formed or otherwise placed on the tray 34a as a guide for correct placement of the containers 22 in the holes 78a, since each appliance 24 in the various containers 22 must normally be affixed to a specific tooth. One end of the setup tray 34a has a hole 80a identical to holes 78a for receiving an open-topped container having a well to dispense etchant. Advantageously, the container for dispensing etchant may be similar to the containers 22, except that the cover, flexible film and dental appliance are not present.

The setup tray 34a also has a recess 82a for receiving a primer tube (not shown) containing a swab predosed with an orthodontic adhesive primer. The primer tube is somewhat similar to the applicator unit assemblies described in U.S. Pat. No. 4,952,204, the disclosure of which is incorporated by reference herein.

The recess 82a includes two tapered apertures 84a that extend completely through the setup tray 34a. The recess 82a also includes a central contoured rib 86a that extends between the apertures 84a below the top of the setup tray 34a. The tray 34a includes wall sections above the rib 86a that are spaced apart a distance sufficient to releasably retain the primer tube in place. To remove the primer tube, the user presses either end of the tube further into the respective aperture 84a in order to cause the primer tube to pivot about the rib 86a. Once pivoted, the tube is exposed so that it may then be grasped by the user and pulled away to release the tube from the wall sections.

The setup tray 34a is made of a cross-linked elastomeric material that has a glass transition temperature below its temperature of use (i.e., below normal expected indoor office ambient air temperatures such as 65°75° F.). The setup tray 34a material preferably has a Shore A hardness in the range of 40–80, and more preferably is 70.

The setup tray 34a is molded of a flexible, natural or synthetic rubber material such as "SILASTIC" brand high strength silicone rubber grade HS-70, or alternatively grade HS-50 (Dow Corning). The setup tray 34a is preferably sterilizable by a dry heat, steam or chemical sterilization process for reuse once empty containers 22 have been removed. The material has sufficient inherent flexibility to releasably retain the containers in the holes 78a, and also to releasably retain the primer tube between the wall sections above the central rib 86a. Further, the material has sufficient weight and presents sufficient frictional resistance to retain the setup tray 34a in place when located on a surface next to the storage cabinet 32 for receiving the containers 22, or when placed next to the patient's chair on a shelf, tray or other surface for application of the dental appliances in the patient's mouth.

As an option, the setup tray 34a may be made of a relatively stiff material that is sterilized for reuse. Suitable stiff materials include plastics such as glass reinforced polyetherimide copolymer ("ULTEM" brand, no. CRS 5201, General Electric) or liquid crystal polymer ("VECTRA" brand, no. A530, Hoechst Celanese). In making the tray 34a of stiff materials, the underside of the tray 34a is hollow, and the holes 78a are slightly larger than that which is described above to avoid the interference fit with the containers 22 and rely substantially on the opposed pair of projections to retain the containers 22 in place.

The setup tray 34b depicted in FIG. 11 is somewhat similar to the setup tray 34a in that the setup tray 34b has a spaced apart series of holes 78b arranged in two rows to receive the containers 22. The recesses 46 snap into the edge of the wall structure surrounding the holes 78b to assist in retaining the containers 22 in the hole 78b. The setup tray 34b also has an additional hole 80b similar to hole 80a in FIG. 10.

The setup tray 34b is made of a 4 mm thick double layer laminate of chip board, with a layer of 0.4 mm thick clay coated solid bleached sulfate paperboard that is folded over all four edges of the chip board laminate. The setup tray 34b is disposed of after a single use along with the containers 22 received therein. The setup tray 34b also has a die cut tab 88b that is folded upward and has an aperture for receiving a neck of the aforementioned primer tube.

The setup tray 34c as shown in FIG. 12 is made of metal (preferably stainless steel) and is curved along its transverse axis for nesting with other similar metal setup trays. The setup tray 34c has two rows of holes 78c to receive containers 22 in snap-fit relation into the recesses 46. Each side of the tray 34c has an elongated recess 81c for receiving a primer tube. Four non-skid feet 83c made of a plastic or synthetic rubber material are fixed to the underside of four corners of the setup tray 34c to assist in restraining movement of the latter when placed on a shelf, tray or other selected location in use, and to facilitate stacking in spaced-apart relation with other, similar trays. Although not shown, the tray 34c preferably has an extra hole similar to holes 80a and 80b shown in FIGS. 10 and 11.

Figure 13:
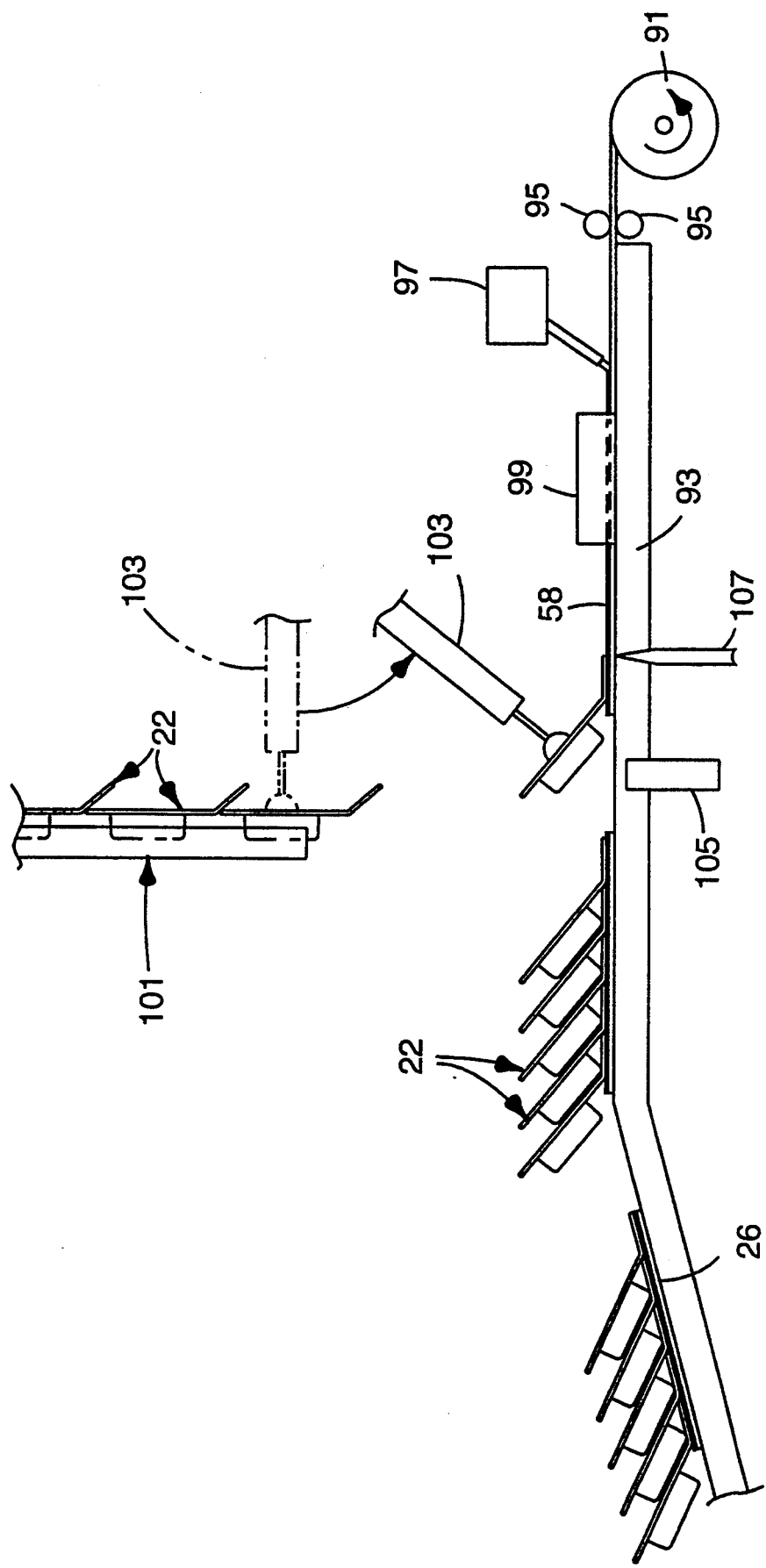
FIG. 13 is a reduced, schematic elevational view illustrating a method of assembling the containers to the carrier strip.

A method for assembling the containers 22 to the carrier strips 26 using the hot melt adhesive 58 is schematically illustrated in FIG. 13 and includes a roll 91 of continuous carrier strip material that is dispensed along a support rail 93 by an opposed pair of pinch drive rollers 95. As the carrier strip material is advanced along the support rail 93, the adhesive 58 is dispensed onto the carrier strip material in a continuous bead (or optionally in the form of a flat ribbon) along the central axis of the carrier strip material by means of a hot melt adhesive pressure dispenser 97. The adhesive 58 is kept in a warmed, softened state as the carrier strip material is advanced by passage of the carrier strip material with the adhesive 58 through a heat retention tunnel 99.

A magazine feeder and storage unit 101 located above the support rail 93 carries a number of the containers 22 each containing one of the appliances 24. A reciprocating arm 103 includes at its outer end a vacuum port that is connected to a source of negative air pressure, and the negative air pressure at the port is controlled in timed sequence with movement of the arm 103. Negative air pressure is applied to the port when the arm 103 is raised to a position adjacent the next container 22 in the feeder and storage unit 101, such that the arm 103 is securely coupled to such container 22. The arm 103 and the supported container 22 then descend toward the carrier strip material.

The arm 103 continues to descend until the tab 52 of the supported container 22 is firmly seated in the softened, semi-viscous hot melt adhesive 58. Next, the negative air pressure is released from the port so that the container 22 detaches from the arm 103. The arm 103 then ascends to meet and support the next container 22 awaiting in the feeder and storage unit 101 and the cycle is repeated.

The carrier strip material continues to advance in timed, step fashion as the arm 103 repeats its cycle of movement. After the tabs 52 of the containers 22 are embedded in the hot melt adhesive 58, advancement of the carrier strip material causes the material, the containers 22 and the adhesive 58 to pass through a cooling zone established by a cooling air source 105. The cooling zone chills the adhesive 58 to cause the adhesive 58 to thereafter retain each container 22 on the carrier strip 26 until such time as the container 22 is pulled from the carrier strip 26 for use.

Movement of a cutoff blade 107 is timed in sequence with movement of the carrier strip material so that the latter is cut into individual carrier strips 26 each supporting five containers 22 once the five containers 22 are set in place in the adhesive 58. Preferably, the support rail 93 declines away from the blade 107, so that the assemblies of the carrier strips 26 and the containers 22 self-descend toward a location for placement in the sales unit carton 28.

Figure 14:
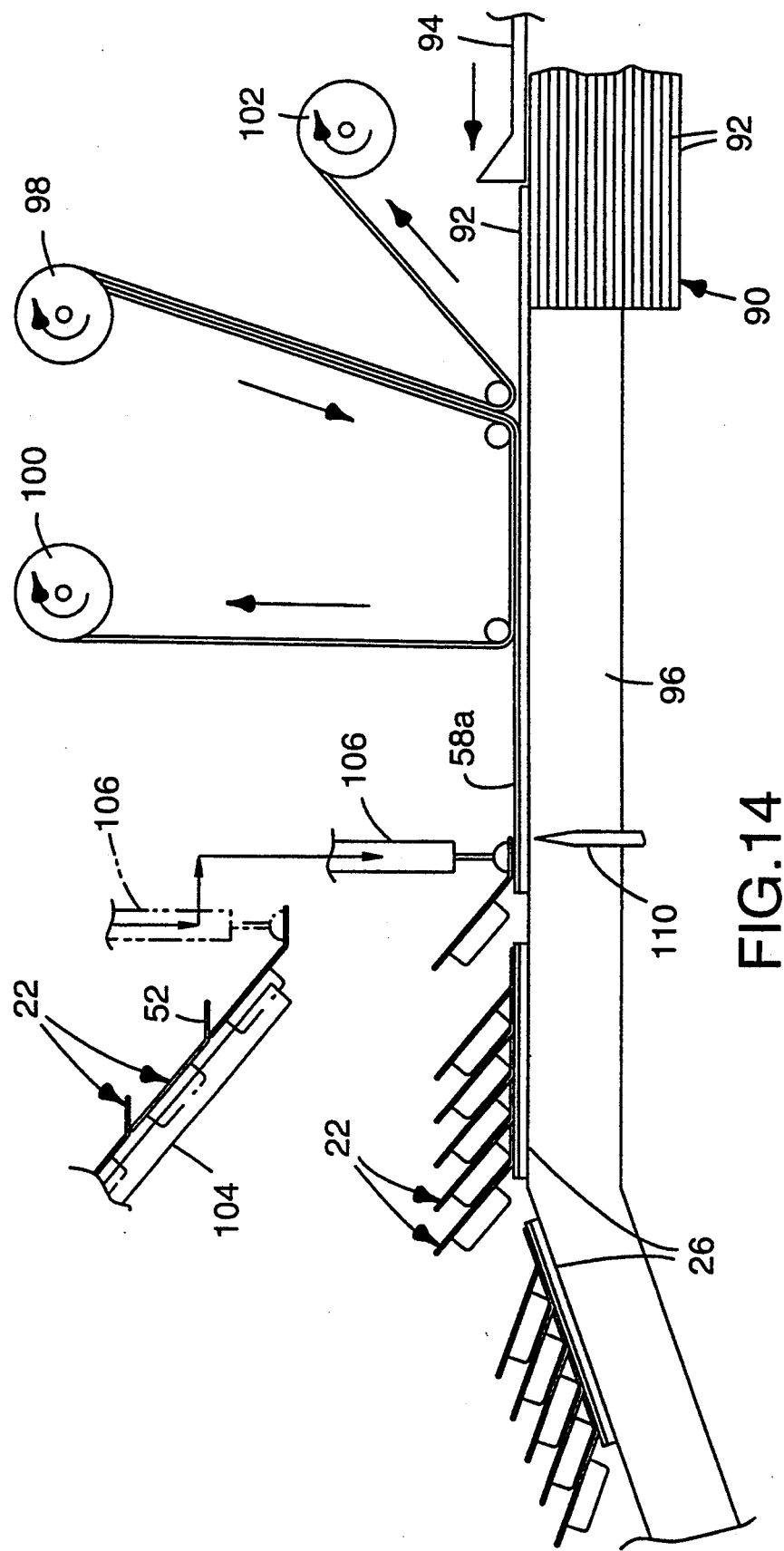
FIG. 14 is a view somewhat similar to FIG. 13 showing another method of assembling the containers to the carrier strip.

A method of assembling the containers 22 to the carrier strip 26 using double sided adhesive tape 58a is schematically illustrated in FIG. 14 and includes a feeder 90 having a stacked magazine of carrier strip blanks 92. Each of the blanks 92 has a length equal to ten carrier strips 26. The feeder 90 also includes a push plate 94 that advances at appropriate timed intervals the next carrier strip blank 92 along a support rail 96. As each blank 92 is advanced along the support rail 96, the double sided pressure sensitive adhesive tape 58a is applied to the upper face of the carrier strip blank 92 from a tape feeder roll 98. Two takeup spools 100, 102 gather release liners that initially cover opposite faces of the tape 58a when on the feeder roll 98.

Individual containers 22 are advanced toward the support rail 96 along a slotted plate 104 until reaching a position wherein the tab 52 of each container 22 is located in front of a movable arm 106 having a port in communication with a source of negative air pressure. As the arm 106 contacts the tab 52, negative air pressure is supplied to the port to enable the container 22 to be coupled and supported by the arm 106. Next, the arm 106 is indexed toward the support rail 96 to guide the tab 52 toward a portion of the exposed face of the double sided tape 58a. The arm 106 continues to advance until the tab 52 is firmly pressed against the tape 58a to affix the container 22 to the carrier strip blank 92. Subsequently, the negative air pressure is released from the port to uncouple the tab 52 from the arm 106, and the arm 106 is then retracted a sufficient distance so that the next container 22 on the plate 104 may be coupled to the arm 106. A cutoff blade 110 is movable in timed relationship to movement of the carrier strip blanks 92, and is operable to cut the blanks 92 into individual carrier strips 26 after five of the tabs 52 have been securely fixed to the carrier strips 26. Although not shown, a feeding mechanism is provided for moving the containers 22 along the plate 104 in timed sequence to movement of the arm 106 and operation of the negative air pressure source. Optionally, a roll feeder similar to the feeder 91 in FIG. 13 may be used to feed continuous carrier strip material instead of the discrete carrier strip blanks 92 described above.

As can be appreciated, the present invention provides a system for enabling the orthodontist to retain a variety of different appliances such as orthodontic brackets in an organized fashion. The storage cabinet 32 is particularly advantageous in that it mates with and may be stacked atop similar cabinets presently used for storing orthodontic bands in many offices. Another advantage is that the organizer tray 30 fits within the confines of drawers of existing modular storage cabinets widely used for bands. Yet, the system enables the orthodontist to readily assemble customized setup trays containing appliances that are appropriate for specific patients. While the system 20 is useful for orthodontic brackets that are precoated with a light curable adhesive, it should be understood in this regard that the containers 22 may be used to hold non-adhesive precoated brackets as well as other dental appliances.

What is claimed is:

1. A dental dispensing system comprising:
    a plurality of dental appliances;
    a plurality of containers each receiving a respective one of said dental appliances;
    a carrier strip;
    means for releasably connecting each of said containers to said carrier strip;
    an organizer tray; and
    structure releasably securing said carrier strip to said organizer tray such that said carrier strip is retained by said tray as one or more of said containers are released from said carrier strip.

2. The system of claim 1 wherein said tray includes opposed channels for slidably receiving said carrier strip.

3. The system of claim 1 wherein said tray includes a bottom wall, a front wall and a pair of opposed channels extending over said bottom wall and perpendicularly away from said front wall, said tray including a slot located between said front wall and said bottom wall and extending between said channels for removal of said carrier strip once said containers have been released from said carrier strip.

4. The system of claim 1 wherein said means for releasably connecting each of said containers to said carrier strip comprises an adhesive.

5. The system of claim 4 wherein said adhesive is a hot melt adhesive.

6. The system of claim 4 wherein said adhesive is part of a double sided adhesive tape.

7. The system of claim 1 wherein each of said containers includes a cover having a tab, and wherein said means for releasably connecting each of said containers to said carrier strip releasably connects said tab to said carrier strip.

8. The system of claim 1 wherein said containers are connected to said carrier strip along a row.

9. The system of claim 8 wherein certain of said containers are in contact with the next adjacent container along said row.

10. The system of claim 1 including a cabinet having a drawer, and wherein said organizer tray is received in said drawer.

11. The system of claim 10 wherein said tray is removably received in said drawer.

12. The system of claim 1 wherein said drawer includes a shoulder for contact with said organizer tray to facilitate retention of said organizer tray in said drawer.

13. The system of claim 1 wherein said organizer tray has ten aligned, side-by-side pairs of opposed channels for slidably receiving said carrier strips, said ten pairs of channels corresponding with ten respective, expected locations of use of said dental appliances in one arch of the mouth.

14. A dental dispensing system comprising:
    a plurality of dental appliances;
    a plurality of containers each having a side wall and a bottom defining a well, said well of each of said containers receiving a respective one of said dental appliances, each of said containers including a cover removably covering its well, each of said containers having a generally flat configuration;
    a carrier strip; and
    means for detachably connecting each of said containers to said carrier strip such that said containers abut each other and are oriented in a stacked array with each of said containers extending in an upward direction.

15. The system of claim 14 wherein said cover of each of said containers includes a tab that extends away from said well for gripping said cover and releasably engages said carrier strip.

16. A dental dispensing system comprising:
    a plurality of dental appliances;
    a plurality of containers each having a sidewall and a bottom defining a well, each of said containers including a cover extending across said well, said cover including an outwardly projecting tab for opening the cover for access to said well, each well receiving a respective one of said dental appliances;
    a carrier strip; and
    a quantity of adhesive detachably connecting said tab of each of said containers to said carrier strip in order to releasably retain each container on said carrier strip, said containers abutting each other and oriented in a stacked array with each of said containers extending in an upward direction.

17. The system of claim 16 wherein said quantity of adhesive is a hot melt adhesive.

18. The system of claim 16 wherein said quantity of adhesive is part of a double sided pressure sensitive adhesive tape located on said carrier strip.

19. The system of claim 16 wherein said carrier strip has a longitudinal axis, and wherein said containers are located in a row along said longitudinal axis.

* * * * *

UNITED STATES PATENT AND TRADEMARK OFFICE
CERTIFICATE OF CORRECTION

PATENT NO. : 5,350,059

DATED : September 27, 1994

INVENTOR(S) : Bruce E. Chester and James D. Cleary

It is certified that error appears in the above-indentified patent and that said Letters Patent is hereby corrected as shown below:

Col. 3, line 60, delete "35".

Col. 4, line 20, insert -- an -- before "intermediate".

Col. 6, line 31, insert -- at -- before "an".

Signed and Sealed this

Eighteenth Day of April, 1995

Attest:

BRUCE LEHMAN

Attesting Officer

*Commissioner of Patents and Trademarks*